(12) United States Patent
Lunsford et al.

(10) Patent No.: US 6,596,912 B1
(45) Date of Patent: Jul. 22, 2003

(54) CONVERSION OF METHANE TO $C_{4+}$ ALIPHATIC PRODUCTS IN HIGH YIELDS USING AN INTEGRATED RECYCLE REACTOR SYSTEM

(75) Inventors: Jack H. Lunsford, Bryan, TX (US); Serguei Pak, Maywood, NJ (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 09/577,008

(22) Filed: May 24, 2000

(51) Int. Cl.[7] .............................. C07C 2/04; C07C 2/08; C07C 2/12
(52) U.S. Cl. .................. 585/316; 585/315; 585/329; 585/330; 585/943
(58) Field of Search .................. 585/315, 316, 585/324, 330, 943

(56) References Cited

U.S. PATENT DOCUMENTS 5,336,825 A 8/1994 Choudhary et al. ......... 585/500

OTHER PUBLICATIONS

Search Results from the RRC Technical Library—"Oxidative Coupling of Methane (Or Natural Gas): Economic Factors Update," 1997–Date, Jun. 3, 1999.
Search Results from the RRC Technical Library—"Oxidative Coupling of Methane (or Natural Gas) to Ethylene: Selectivity, Yield, Operating Conditions; Dehydrogenation", Jun. 3, 1999.
Search Results: "Oxidative Coupling: Economic Factors", Aug. 6, 1997.

*Primary Examiner*—Thuan D. Dang
(74) *Attorney, Agent, or Firm*—Baker Botts L.L.P.

(57) ABSTRACT

This invention relates to processes and systems for the conversion of methane in high yields to $C_{4+}$ hydrocarbons. The principal steps of the recycle process include reacting methane and $O_2$ in an oxidative coupling reactor over a $Mn/Na_2WO_4/SiO_2$ catalyst at 800° C. to convert the methane to ethylene, and oligomerizing the ethylene product by reacting it with an H-ZSM-5 zeolite catalyst at 275° C. in a catalytic reactor for subsequent conversion of the ethylene to higher hydrocarbons. Total yields of $C_{4+}$ products using the process of the invention are in the range of about 60% to about 80%, and yields of $C_{4+}$ nonaromatic hydrocarbons are in the range of about 50% to about 60%.

30 Claims, 3 Drawing Sheets

CONVERSION OF METHANE TO $C_{4+}$ ALIPHATIC PRODUCTS IN HIGH YIELDS USING AN INTEGRATED RECYCLE REACTOR SYSTEM

BACKGROUND OF THE INVENTION

1. Field of the Invention

This invention relates to the conversion of methane to $C_{4+}$ products in high yields, and, in particular, to methods and systems for the steady state conversion of methane to $C_{4+}$ aliphatic products in high yields using an integrated recycle reactor.

2. Description of the Background

Several recent studies have demonstrated that product yields approaching 70% may be achieved during the oxidative coupling of methane (OCM) by employing a recycle reactor with continuous removal of ethylene (Y. Jiang et al., Science 264:1563, 1994; R. B. Hall et al., ACS Div. Petr. Chem. Prepr. 39(2):214, 1994; E. M. Cordi et al., Appl. Catal. A: Gen. 155:L1–L7, 1997; A. Mashocki, Appl. Catal. A: General 146:391, 1996). The ethylene may either be directly separated from the recycle stream or it may be converted to another product, which is subsequently separated. As an example of the former, $Ag^+$ ions have been used to facilitate the transport of ethylene and a small amount of propylene through a membrane contactor. The olefins were recovered in nearly pure form by heating the aqueous silver-olefin complexes to 100° C. As an example of the second alternative, the ethylene was converted to aromatics (mainly benzene and toluene) over a Ga/H-ZSM-5 zeolite. The aromatics were separated from the recycle stream by cryogenic means.

However, in both of these cases, chemicals rather than fuels were produced. With respect to the utilization of methane in large remote gas fields, it is desirable to form a liquid transportation fuel that has a minimal amount of aromatics.

A two-step process for converting methane to liquid hydrocarbons in the gasoline range using oxidative coupling over a catalyst, followed by passing the product stream over a solid acid catalyst has been described (U.S. Pat. No. 5,336,825 to Choudhary et al.). However, this process does not recycle unreacted methane and ethane and produces products in low yields.

There is therefore a need for systems and methods for converting methane in high yields to $C_{4+}$ nonaromatic hydrocarbons.

SUMMARY OF THE INVENTION

The present invention overcomes the problems and disadvantages associated with current strategies and designs and provides systems and processes for converting methane in high yields to $C_{4+}$ nonaromatic hydrocarbons, producing high yields of hydrocarbons in the $C_{4+}$ range.

Accordingly, one embodiment of the invention is directed to a process or method for producing $C_{4+}$ aliphatic hydrocarbons in high yields from methane comprising the steps of: providing a stream of methane and a stream of $O_2$; conveying the stream of methane and stream of $O_2$ to an oxidative coupling reactor (OCM reactor), for the oxidative coupling of methane; converting the methane to ethylene and other by-products in the oxidative coupling reactor, thereby forming an ethylene-containing product stream; conveying the ethylene-containing product stream to a catalytic reactor; oligomerizing the ethylene in the catalytic reactor by reacting the ethylene over an acidic pentasil zeolite catalyst to produce an end product-containing stream, the end product-containing stream comprising hydrocarbons having four or more carbons; removing the hydrocarbons having four or more carbons from the end product-containing stream leaving an effluent stream; and recycling the effluent stream through the oxidative coupling reactor.

Another embodiment of the invention is directed to a process or method for producing $C_{4+}$ hydrocarbons in high yields from methane comprising the steps of: reacting methane and $O_2$ in an oxidative coupling reactor to produce a first product stream, the first product stream comprising ethylene; reacting the first product stream in a catalytic reactor in the presence of an acidic pentasil zeolite catalyst to produce a second product stream, the second product stream comprising $C_{4+}$ hydrocarbons; removing $C_{4+}$ hydrocarbons from the second product stream leaving an effluent stream; and recycling the effluent stream through the oxidative coupling reactor.

Another embodiment is directed to a system for producing $C_{4+}$ hydrocarbons in high yields from methane comprising: an oxidative coupling reactor, the oxidative coupling reactor adapted to receive methane and $O_2$ and to convert the methane to a first product stream, the first product stream containing ethylene; a catalytic reactor containing an acidic pentasil zeolite catalyst disposed downstream from the oxidative coupling reactor for receiving the first product stream and converting it to a second product stream, the second product stream containing $C_{4+}$ hydrocarbons; means for removing $C_{4+}$ hydrocarbons from the second product stream to produce an effluent stream; and means for recycling the effluent stream to the oxidative coupling reactor. Preferably, the apparatus further comprises means for removing water from the first product stream, means for removing $CO_2$ from the first product stream, and means for removing by-products from the first product stream.

Other embodiments and advantages of the invention are set forth in part in the description which follows, and in part, will be obvious from this description, or may be learned from the practice of the invention.

DESCRIPTION OF THE INVENTION

As embodied and broadly described herein, the present invention is directed to the production of $C_{4+}$ products from methane in high yields. Specifically, the present invention is directed to methods for the steady state conversion of methane to $C_{4+}$ aliphatic products in high yields using an integrated recycle reactor system. The invention is also directed to a recycle reactor system for use in the production of $C_{4+}$ aliphatic products from methane in high yields. The present invention allows for total yields of $C_{4+}$ products in the range of about 60% to 80%, and yields of $C_{4+}$ nonaromatic hydrocarbons in the range of about 50% to 60%.

Specifically, it has been discovered that methane can be converted in high yields to $C_{4+}$ nonaromatic hydrocarbons using a recycle system. In a preferred embodiment, the principal components of the recycle system include an oxidative coupling reactor with a $Mn/Na_2WO_4/SiO_2$ catalyst at 800° C. for conversion of methane to ethylene, and a reactor with an H-ZSM-5 zeolite catalyst at 275° C. for subsequent conversion of ethylene to higher hydrocarbons. $C_{4+}$ hydrocarbons are condensed and removed and the effluent or recycle stream is recycled through the system.

Figure 1:
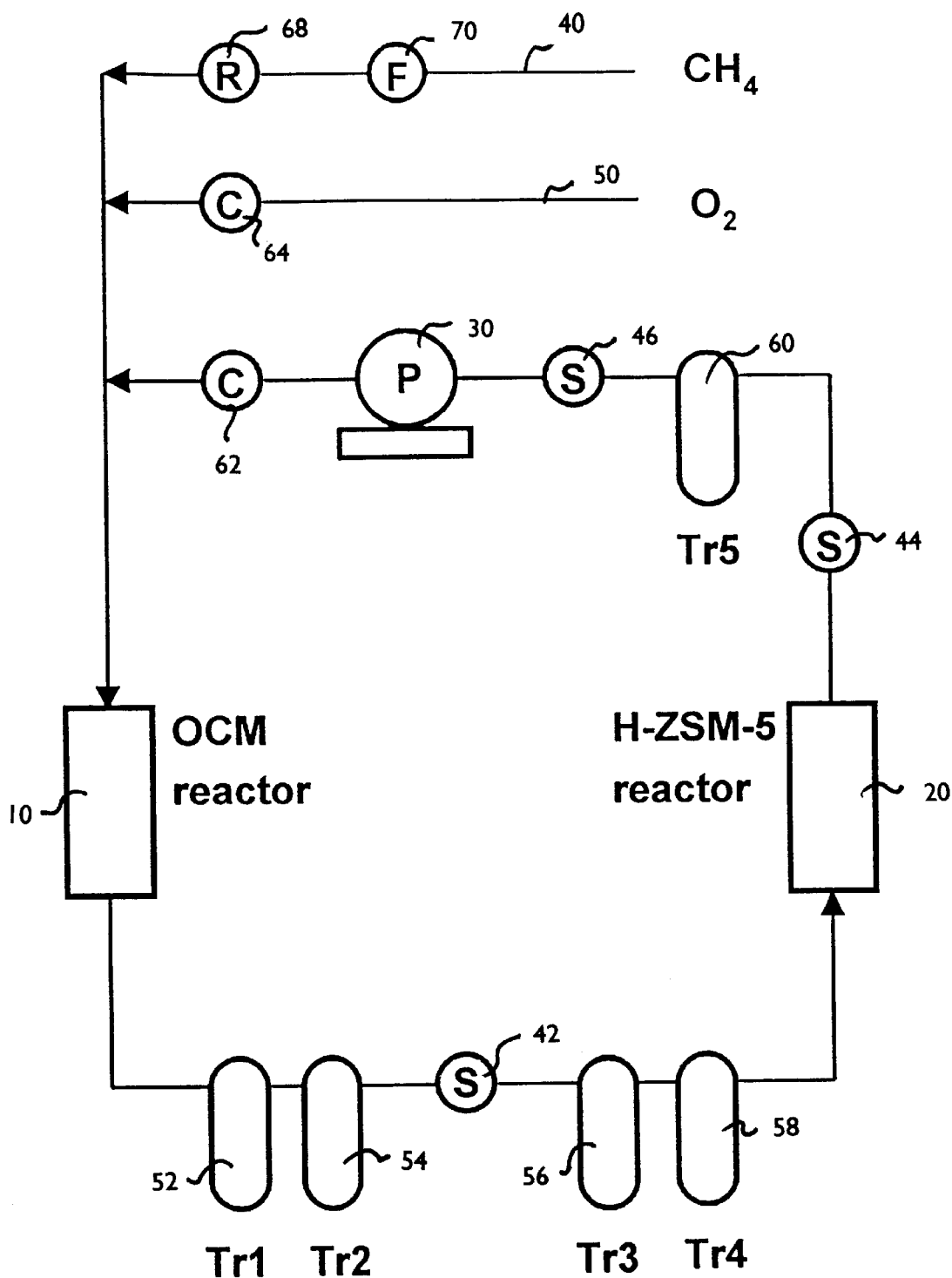
FIG. 1 is a schematic diagram of an integrated recycle system according to one embodiment of the invention.

A preferred embodiment of a reactor system for use in the invention is depicted in FIG. 1. Referring to FIG. 1, recycle system 1 comprises two sequential reactors, a first OCM reactor 10 and a second reactor 20, which contains an H-ZSM-5 catalyst. Recycle system 1 also includes a metal bellows (gas recycle) pump 30 for gas recycling, $CH_4$ inlet 40 and $O_2$ inlet 50 for continuous admission of $CH_4$ and $O_2$ reactants, gas sampling ports 42, 44 and 46, and traps 52, 54, 56, 58 and 60 for removing certain products of the reaction. The recycle and oxygen flow rates are controlled and maintained at a constant value by recycle mass flow controller 62 and oxygen flow mass flow controller 64. Preferably, the recycle flow rate is between about 58 and 145 ml/min and the oxygen flow rate is between about 6.5 and 19.5 ml/min. The rate of methane entering the system is controlled by a pressure regulator 68. Preferably, methane is added at a rate necessary to maintain a constant pressure. Methane flow is monitored by flowmeter 70. At a constant total pressure in the recycle system, the flow of methane is equal to the rate of methane conversion to products.

Several in-line traps are preferably provided to allow removal of various reaction products. A first trap 52 at 0° C., located downstream from the OCM reactor, is a water removal trap and is used to decrease the water partial pressure to 2.4 Torr. A second trap 54, containing KOH at room temperature, is a $CO_2$ removal trap and allows for the continuous removal of the $CO_2$ by-product. A third trap 56, containing silica gel, followed by a fourth trap 58 at −72° C. (ethanol/$CO_2$ (dry ice) slush), are used to remove minor by-products of the OCM reaction. Although the concentration of these products is typically below detection limits, they affect the stability of the zeolite catalyst. Without these traps, the conversion of ethylene over the H-ZSM-5 zeolite was found to decrease to less than 90% within 4 hours. With the traps in place, however, the conversion of ethylene remains greater than 90% for up to 10 hours.

A fifth trap 60, maintained at −94° C. by hexane slush, is located downstream from reactor 20 to condense $C_{4+}$ hydrocarbons.

As set forth in Example 3, below, the effectiveness for removal of $C_{4+}$ products according to the method of the invention depends on the recycle flow rate and the overall condensation rate. The present invention allows for the efficiency of $C_{4+}$ removal in the range of about 45% to 75%. The $C_{4+}$ products that are not condensed are composed mainly of butane isomers. These isomers, together with hydrocarbons containing fewer than four carbon atoms are recycled over the OCM catalyst and are converted to olefins which subsequently, together with ethylene, are oligomerized.

If desired, a third reactor containing a $Cr_2O_3/\alpha\text{-}Al_2O_3$ catalyst may be placed after OCM reactor 10 and before reactor 20 to convert ethane to ethylene. This third reactor preferably operates at a temperature of 900° C.

The recycling system of the present invention provides superior yields to the single pass systems known in the art. The conversions and selectivities obtained over the OCM catalyst in a single pass reactor have been described (E. M. Cordi et al., Appl. Catal. A: Gen. 155:L1–L7, 1997; P. Qui et al., Catalysis Letters, 48:11–15, 1997; D. Wang et al., J. Catal., 155:390, 1995). In the single-pass (non-recycle) mode, a $CH_4$ conversion level of only 20% and a $C_{2+}$ product selectivity of 80% can be attained for periods up to 100 hours when the reaction is carried out at 800° C. with a $CH_4/O_2$ ratio of 7.4. This conversion and selectivity corresponds to a $C_{2+}$ yield of 16%. The ethylene-to-ethane ratio is 1.3. In contrast, the present invention allows for much higher yields of $C_{4+}$. Further, the system produces only limited amounts of aromatics, an important advantage in view of EPA limitations on the amount of permissible aromatics in gasoline.

Figure 2:
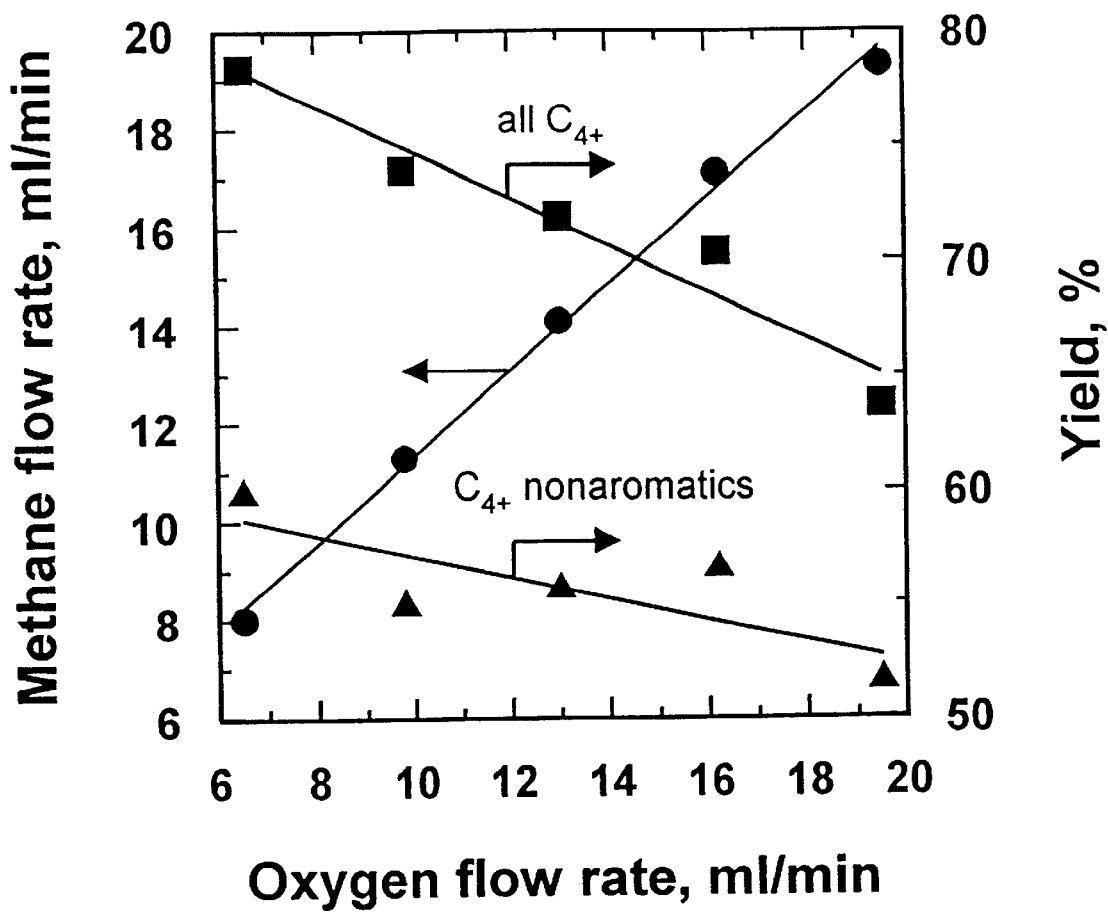
FIG. 2 is a graph showing the effect of oxygen flow rate on methane reaction rate and yield of products at a total recycle rate of 116 ml/min.

For example, as shown in FIG. 2, $C_{4+}$ nonaromatic yields approaching 60% and total $C_{4+}$ yields approaching 80% were achieved with the recycle reactor. These yields may be compared with an ethylene yield of about 8% in the single-pass reactor over same catalyst. The ethylene yield may be improved somewhat by using a second dehydrogenation catalyst, but it never reaches more than about 14%.

Accordingly, one embodiment of the invention is directed to methods and processes for the steady state conversion of methane to $C_{4+}$ aliphatic hydrocarbons in high yields using a recycling system. One such embodiment is directed to a process for producing $C_{4+}$ aliphatic hydrocarbons in high yields from methane comprising the steps of: providing a stream of methane and a stream of $O_2$; conveying the stream of methane and stream of $O_2$ to an oxidative coupling reactor; converting the methane to ethylene and other by-products, including ethane, in the oxidative coupling reactor, thereby forming an ethylene-containing product stream; conveying the ethylene-containing product stream to a catalytic reactor; oligomerizing the ethylene in the catalytic reactor by reacting the ethylene over an acidic pentasil zeolite catalyst to produce an end product-containing stream, the end product-containing stream comprising hydrocarbons having four or more carbons, as well as hydrocarbons having one to three carbons; removing the hydrocarbons having four or more carbons from the end product-containing stream leaving an effluent stream; and recycling the effluent stream through the oxidative coupling reactor.

Preferably, the stream of methane and stream of $O_2$ are mixed prior to conveying to the oxidative coupling reactor. Preferably, methane is added as it is consumed at the rate necessary to maintain a constant pressure in the system (e.g., 15 ml/min), and the methane flow rate is equal to the rate of methane conversion. The process is preferably performed at a system pressure of between about 1 atm and about 10 atm, more preferably, between about 1 atm and about 5 atm, and most preferably, at a pressure of about 5 atm.

The oxidative coupling reactor may be any suitable reactor, such as a fixed bed or a fluidized bed reactor. Preferably, the reactor is a fluidized bed reactor. The reactor is lined with an inert material such as alumina or fused quartz. Most preferably, the lining is alumina. A suitable catalyst is provided in the reactor to facilitate or catalyze conversion of methane to ethylene. Suitable catalysts include $SrO/La_2O_3$, $BaO/MgO$ and $Mn/Na_2WO_4SiO_2$. However, in a preferred embodiment, the catalyst is a $Mn/Na_2WO_4/SiO_2$ catalyst, and most preferably, a $Mn(2\ wt\%)/Na_2WO_4(5\ wt\%)/SiO_2$ catalyst.

The temperature of the oxidative coupling reactor is preferably maintained at a temperature of between about 750° C. and about 980° C., and more preferably, between about 775° C. and about 825° C. Most preferably, the step of converting the methane to ethylene in the oxidative coupling reactor takes place at a temperature of about 800° C.

The methane is converted in the oxidative coupling reactor to produce an ethylene-containing product stream, containing ethylene and other products, as indicated in the following reaction:

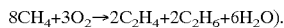

$$8CH_4 + 3O_2 \rightarrow 2C_2H_4 + 2C_2H_6 + 6H_2O).$$

The ethylene-containing product stream is transferred to the catalytic reactor for oligomerization. The catalytic reactor may be any suitable reactor, such as an alumina tube. Preferably, the reactor is a fluidized bed or a fixed bed reactor. Useful catalysts include acidic pentasil zeolites with high silica-to-alumina ratios. Most preferably, the catalyst in the catalytic reactor is H-ZSM-5 zeolite, having a Si/Al ratio of 28.5. The reaction in the catalytic reactor produces an end-product stream containing $C_{4+}$ aliphatic hydrocarbons and other products.

Mobil H-ZSM-5 zeolite is the preferred catalyst for ethylene oligomerization. This catalyst demonstrates high activity and good selectivity in the reaction of ethylene to higher hydrocarbons. Using a model mixture of 3.3% ethylene in nitrogen, optimum conditions were determined for the production of $C_{4+}$ aliphatics. In a temperature range of 271–279° C., the conversion was 85–88% with a maximum selectivity of approximately 86% towards nonaromatic hydrocarbons.

As noted, the partially deactivated zeolite catalyst is easily regenerated. Accordingly, if desired, the process may optionally comprise the step of regenerating the zeolite catalyst in flowing $O_2$ at about 450° C. for sufficient time to restore activity.

Preferably, the reaction in the catalytic reactor is performed at a temperature of between about 250° C. and about 350° C., and more preferably, at a temperature of between about 260° C. and about 280° C. Most preferably, the ethylene is reacted in the catalytic reactor at a temperature of about 275° C.

Preferably, the process further comprises removing water after the step of converting to decrease water partial pressure to about 2.4 Torr. This may be accomplished any number of ways, including the addition of a drying agent such as calcium sulfate or the use of a trap at 0° C. For example, in a preferred embodiment, water is removed using a trap at 0° C. disposed downstream from the oxidative coupling reactor.

The process may further comprise removing $CO_2$ after the step of converting, and more preferably, after the step of removing water. $CO_2$ may be removed any number of ways, such as by absorption in an amine solution or using a trap containing KOH. For example, in a preferred embodiment, the $CO_2$ is removed by a trap containing KOH at room, temperature disposed downstream from the oxidative coupling reactor and the water trap.

The process may further comprise removing organic residue or trace by-products of the oxidative coupling by providing a trap containing silica gel after converting the methane to ethylene and preferably after removing water and $CO_2$. By-products of the oxidative coupling reaction removed by the silica gel include trace amounts of high molecular weight hydrocarbon products. The process may further comprise removing by-products after converting methane to ethylene by providing a trap containing ethanol/$CO_2$ slush gel downstream of the silica gel trap. By-products removed by the ethanol/$CO_2$ slush gel trap include any remaining water and undesirable by-products of the OCM reaction.

The effluent stream may be recycled at any desired rate. However, the effluent stream is preferably recycled at a recycle ratio of between 3 and 15, more preferably at a recycle ratio of between 5 and 10, and most preferably, at a recycle ratio of about 8.6. As used herein, a recycle ratio of 8.6 means the amount of methane recycled is about 8.6 times the amount of methane added to the system.

Optimally, the process of the invention produces a total yield of $C_{4+}$ products in the range of about 60% to about 80% and a total yield of $C_{4+}$ nonaromatic hydrocarbons in the range of about 50% to about 60%.

Another embodiment of the invention is directed to a process for producing $C_{4+}$ hydrocarbons in high yields from methane comprising the steps of: reacting methane and $O_2$ in an oxidative coupling reactor to produce a first product stream, the first product stream comprising ethylene; reacting the first product stream in a catalytic reactor in the presence of a first catalyst to produce a second product stream, the second product stream comprising $C_{4+}$ hydrocarbons and wherein the first catalyst is an acidic pentasil zeolite catalyst; removing $C_{4+}$ hydrocarbons from the second product stream leaving an effluent stream; and recycling the effluent stream through the oxidative coupling reactor. A second catalyst, preferably a $Mn/Na_2WO_4/SiO_2$ catalyst, is provided in the oxidative coupling reactor.

Another embodiment of the invention is directed to a system or apparatus for producing $C_{4+}$ hydrocarbons in high yields from methane comprising: an oxidative coupling reactor, the oxidative coupling reactor adapted to receive methane and $O_2$ and to convert the methane to a first product stream, the first product stream containing ethylene; a catalytic reactor containing an acidic pentasil zeolite catalyst disposed downstream from, and fluidly coupled to, the oxidative coupling reactor for receiving the first product stream and converting it to a second product stream, the second product stream containing $C_4+$ hydrocarbons; means for removing $C_{4+}$ hydrocarbons from the second product stream to produce an effluent stream; and means for recycling or returning the effluent stream to the oxidative coupling reactor. Preferably, the apparatus further comprises means for removing water from the first product stream, means for removing $CO_2$ from the first product stream, and means for removing trace by-products from the first product stream. These means include, but are not limited to, the various traps described above.

The results achieved according to the invention, as set forth in the examples below, demonstrate that a recycle system may be successfully utilized for the production of nonaromatic hydrocarbons in the $C_{4+}$ range in high yields. The data show that 100% methane conversion may be achieved with up to 60% $C_{4+}$ nonaromatic product yield. By significantly increasing the pressure of the system, the molar conversion should increase and the partial pressures of the products should increase. This would greatly facilitate separation processes.

The following examples are offered to illustrate embodiments of the invention, and should not be viewed as limiting the scope of the invention.

EXAMPLES

Example 1

Conversion of Methane to $C_4+$ Aliphatic Products

In this example, the recycling system of FIG. 1 was used to convert methane to $C_{4+}$ aliphatic products.

For the OCM reaction, a Mn(2 wt %)/Na$_2$WO$_4$(5 wt %)/SiO$_2$ catalyst was used. The preparation of the catalyst has been described (D. Wang et al., J. Catal., 155:390, 1995). From 400 to 600 mg of this material with 20–40 mesh size was placed in an alumina reactor with an ID of 6 mm. The temperature of the OCM reactor during the experiments was kept at 800° C.

Ethylene conversion to higher hydrocarbons was carried out in a Pyrex reactor with an ID of 25 mm. Six grams of Mobil H-ZSM-5 zeolite (MZ-1224, Si/Al ratio=28.5) were used for ethylene oligomerization. The temperature of the reactor was 275° C. The zeolite gradually deactivated, and after 8 hours, the conversion of ethylene from the OCM reactor was 90%. Following deactivation to this level, the zeolite was regenerated in flowing oxygen for 3 hours at 450° C., which completely restored the activity of the catalyst.

Analysis of the products of the reaction was carried out by GC using two types of columns. The $C_1$ to $C_4$ hydrocarbons were determined with a Hayesep D column, and the higher carbon number aliphatic and aromatic products were analyzed with a 10% 1,2,3-tris(2-cyanoethoxy)propane (TCEP) on 100/120 Chromosorb column. Thus, the complete product distribution was obtained, including high and low boiling compounds, as well as the selectivities for nonaromatic products.

Example 2

Effect of Varying Oxygen Inlet Flow Rate

Two types of experiments were conducted in the recycle system. While keeping the temperature of the OCM catalyst at 800° C. and the zeolite catalyst at 275° C., the effects of varying the oxygen concentration and recycle rate were studied. The results obtained by varying the oxygen inlet flow rate at a fixed recycle rate of 116 ml/min are given in FIG. 2 and Table 1. FIG. 2 is a graph showing the effect of oxygen flow rate on methane reaction rate (methane flow rate) and yield of products at a total recycle rate of 116 ml/min.

In FIG. 2, the y axis on the left is the methane flow rate in ml/min, the x axis is the oxygen flow rate in ml/min, and the y axis on the right is the % yield of either all $C_4+$ products or $C_{4+}$ nonaromatic products. The squares represent the % yield of all $C_4+$, including aromatics, the triangles represent the % yield of only $C_{4+}$ nonaromatics (i.e., aliphatic products), and the circles represent methane flow rate.

TABLE 1

Effect of Oxygen Flow Rate[a]

| $O_2$ rate[b] ml/min | CH$_4$ rate in ml/min to | | | | | | | | | | $C_{4+}$ nonarom./arom. selectivity ratio |
|---|---|---|---|---|---|---|---|---|---|---|---|
| | CO$_2$ | C$_4$ | C$_5$ | C$_6$[c] | C$_{7+}$[c] | benz. | tol. | xyl. | C$_{10}$ arom. | total arom. | |
| 6.5 | 1.73 | 1.61 | 1.45 | 0.78 | 0.90 | 0.04 | 0.35 | 0.45 | 0.63 | 1.39 | 3.2 |
| 9.8 | 2.95 | 2.29 | 2.07 | 1.11 | 0.72 | 0.04 | 0.36 | 0.60 | 1.02 | 2.15 | 2.9 |
| 13.0 | 3.97 | 2.91 | 2.65 | 0.96 | 1.31 | 0.03 | 0.43 | 0.67 | 1.07 | 2.30 | 3.4 |
| 16.2 | 5.04 | 3.92 | 3.34 | 1.80 | 0.59 | 0.04 | 0.41 | 0.67 | 1.06 | 2.36 | 4.1 |
| 19.5 | 7.01 | 3.98 | 3.41 | 1.75 | 0.79 | 0.04 | 0.38 | 0.65 | 1.12 | 2.37 | 4.2 |

[a]Recycle rate - 116 ml/min, 0.69 g of Mn/Na$_2$WO$_4$/SiO$_2$ at 800° C. 6 g of H-ZSM-5 at 275° C.
[b]1 ml/min (STP) corresponds to 44.6 μmol/min
[c]Nonaromatic $C_6$ and $C_{7+}$ As shown in Table 1 and FIG. 2, the overall effect is that the methane conversion rate, which is equivalent to the methane flow rate, increases with increased oxygen flow rate, but the yield of condensed hydrocarbons, including nonaromatics, decreases. The decrease in the yield of desired products results from the fact that more methane was converted to $CO_2$ as the oxygen concentration increased. Because all oxygen was consumed in the OCM reactor, it did not influence the ratio of nonaromatics to aromatics formed in the second reactor.

The rates at which $CH_4$ was converted to $CO_2$ and to the desired hydrocarbons are given in Table 1. Among the $C_4$ products, the ratio of iso-butane:n-butane:1-butane+1,3-butadiene was approximately 1:0.59:0.26. The aromatic portion was mainly composed of toluene, xylenes and $C_{10}$ aromatic compounds, with only trace amounts of benzene.

As shown in FIG. 2, $C_{4+}$ nonaromatic yields approaching 60% and total $C_4+$ yields approaching 80% can be achieved with the recycle reactor. These yields may be compared with an ethylene yield of about 8% in the single-pass reactor over same catalyst. The ethylene yield may be improved in a single-pass reactor somewhat by using a second dehydrogenation catalyst, but it never reaches more than about 14%.

Example 3

Effect of Recycle Rate

Figure 3:
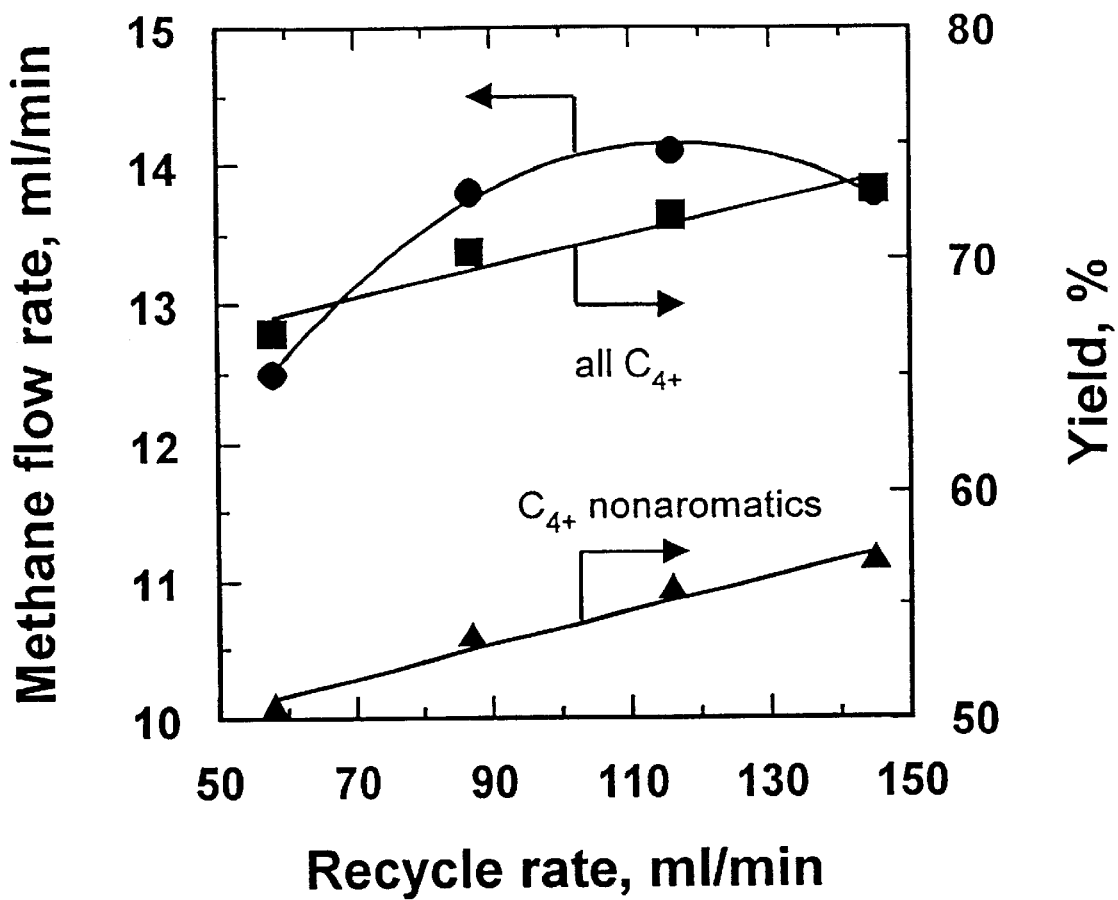
FIG. 3 is a graph showing the effect of recycle rate on methane reaction rate and yield of products at an $O_2$ flow rate of 13.0 ml/min.

The effect of the recycle rate on system performance is shown in FIG. 3 and in Table 2. FIG. 3 is a graph showing the effect of recycle rate on methane reaction rate (methane flow rate) and yield of products at an $O_2$ flow rate of 13.0 ml/min. In FIG. 3, the y axis on the left is the methane flow rate in ml/min, the x axis is the effluent recycle rate in ml/min, and the y axis on the right is the % yield of either all $C_{4+}$ products or $C_{4+}$ nonaromatic products. The squares represent the % yield of all $C_4+$, including aromatics, the triangles represent the % yield of only $C_{4+}$ nonaromatics (i.e., aliphatic products), and the circles represent methane flow rate.

TABLE 2

Effect of Recycle Rate[a]

| Recycle Rate ml/min | $CH_4$ rate[b] in ml/min to | | | | | | | | | | $C_{4+}$ nonarom./arom. selectivity ratio |
|---|---|---|---|---|---|---|---|---|---|---|---|
| | $CO_2$ | $C_4$ | $C_5$ | $C_6$[c] | $C_{7+}$[c] | benz. | tol. | xyl. | $C_{10}$ arom. | total arom. | |
| 58 | 4.14 | 2.86 | 1.63 | 1.02 | 0.79 | 0.06 | 0.54 | 0.53 | 0.75 | 2.05 | 3.1 |
| 87 | 4.08 | 2.82 | 2.45 | 1.46 | 0.63 | 0.03 | 0.40 | 0.62 | 1.06 | 2.31 | 3.2 |
| 116 | 3.97 | 2.91 | 2.65 | 0.96 | 1.31 | 0.03 | 0.43 | 0.67 | 1.07 | 2.30 | 3.4 |
| 145 | 3.73 | 2.16 | 2.61 | 1.30 | 1.79 | 0.04 | 0.37 | 0.64 | 1.06 | 2.21 | 3.6 |

[a]$O_2$ flow rate - 13.0 ml/min, 0.69 g of $Mn/Na_2WO_4/SiO_2$ at 800° C. 6 g of H-ZSM-5 at 275° C.
[b]1 ml/min (STP) corresponds to 44.6 μmol/min
[c]Nonaromatic $C_6$ and $C_{7+}$ The results indicate that the methane conversion rate reaches a maximum at a recycle rate of about 120 ml/min, which corresponds to a recycle ratio of 8.6. The occurrence of a maximum may be related to the fact that an increase in the recycle rate influenced very significantly the condensation efficiency of the light hydrocarbons, especially the $C_4$ products, as can be seen from Table 2. Untrapped hydrocarbons are returned to the OCM reactor where they consume $O_2$ as they are dehydrogenated or converted to $CO_2$. As a result, the consumption of methane decreases since $O_2$ is the limiting reagent. Although part of the $C_4$ hydrocarbons and all of the unreacted $C_2$ and $C_3$ hydrocarbons were recycled through the OCM catalyst, the yields of $C_{4+}$ hydrocarbons continue to increase with increasing recycle rate. This observation implies that the selectivity for the oxidative dehydrogenation of paraffins to olefins, particularly the selectivity for ethylene formation from ethane, is very high over the OCM catalyst. $Mn/Na_2WO_4/SiO_2$ is a very effective catalyst for the oxidative dehydrogenation of ethane (Y. Lin et al., Stud. Surf. Sci. Catal., 119:593, 1998). As shown in Table 2, the ratios of nonaromatics to aromatics were within the same range as those observed when the oxygen inlet flow was varied (Table 1).

Other embodiments and uses of the invention will be apparent to those skilled in the art from consideration of the specification and practice of the invention disclosed herein. For instance, although various flow rates have been provided by way of example, as will be clear to those of skill in the art, the processes of the invention may be scaled up as needed using similar ratios, to produce products in commercial quantities. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A process for producing $C_{4+}$ aliphatic hydrocarbons in high yields from methane comprising the steps of:
   providing a stream of methane and a stream of $O_2$;
   conveying the stream of methane and stream of $O_2$ to an oxidative coupling reactor;
   converting the methane to ethylene in the presence of a catalyst comprising Mn, $Na_2WO_4$, and $SiO_2$ in the oxidative coupling reactor thereby producing an ethylene-containing product stream;
   conveying the ethylene-containing product stream to a catalytic reactor;
   oligomerizing the ethylene in the catalytic reactor by reacting the ethylene over an acidic pentasil zeolite catalyst to produce an end product-containing stream, said end product-containing stream comprising hydrocarbons having four or more carbons;
   removing the hydrocarbons having four or more carbons from the end product-containing stream leaving an effluent stream; and
   recycling the effluent stream through the oxidative coupling reactor.

2. The process of claim 1 wherein the stream of methane and stream of $O_2$ are mixed prior to conveying to the oxidative coupling reactor.

3. The process of claim 1 wherein the catalyst in the oxidative coupling reactor is a Mn(2 wt %)/$Na_2WO_4$(5 wt %)/$SiO_2$ catalyst.

4. The process of claim 1 wherein the converting of methane to ethylene in the oxidative coupling reactor takes place at a temperature of between about 775° C. and about 825° C.

5. The process of claim 1 wherein the converting of methane to ethylene in the oxidative coupling reactor takes place at a temperature of about 800° C.

6. The process of claim 1 wherein said process produces a total yield of $C_{4+}$ nonaromatic hydrocarbons in the range of about 50% to about 60%.

7. The process of claim 1 wherein the acidic pentasil zeolite catalyst in the catalytic reactor is H-ZSM-5 zeolite.

8. The process of claim 7 wherein the H-ZSM-5 zeolite has a Si/Al ratio of 28.5.

9. The process of claim 1 wherein the ethylene is reacted in the catalytic reactor at a temperature of between about 260° C. and about 280° C.

10. The process of claim 1 wherein the ethylene is reacted in the catalytic reactor at a temperature of about 275° C.

11. The process of claim 1 wherein said process produces a total yield of $C_{4+}$ products in the range of about 60% to about 80%.

12. The process of claim 1 further comprising regenerating the acidic pentasil zeolite catalyst in flowing $O_2$ at about 450° C. for sufficient time to restore activity.

13. The process of claim 1 wherein the stream of methane is provided at a flow rate to maintain a constant pressure, wherein said flow rate is equal to the rate of methane conversion.

14. The process of claim 1 further comprising removing water from the ethylene-containing product after the step of converting, to decrease water partial pressure to about 2.4 Torr.

15. The process of claim 1 further comprising removing $CO_2$ from the ethylene-containing product after the step of converting.

16. The process of claim 1 further comprising providing a trap containing silica gel after the step of converting.

17. The process of claim 1 further comprising providing a trap containing ethanol/$CO_2$ slush gel after the step of converting.

18. The process of claim 1 wherein the effluent stream is recycled at a recycle ratio of about 8.6.

19. The process of claim 1 wherein the process is performed at a pressure of between about 1 atm and about 10 atm.

20. A process for producing $C_{4+}$ hydrocarbons in high yields from methane comprising the steps of:

reacting methane and $O_2$ in the presence of a first catalyst comprising Mn, $Na_2WO_4$, and $SiO_2$ in an oxidative coupling reactor to produce a first product stream, said first product stream comprising ethylene;

reacting said first product stream in a catalytic reactor in the presence of a second catalyst to produce a second product stream, said second product stream comprising $C_{4+}$ hydrocarbons;

removing $C_{4+}$ hydrocarbons from the second product stream leaving an effluent stream; and recycling the effluent stream through the oxidative coupling reactor.

21. The process of claim 20 wherein said second catalyst comprises an acidic pentasil zeolite catalyst.

22. The process of claim 21 wherein said $C_{4+}$ hydrocarbons comprise $C_{4+}$ hydrocarbons produced from the oligomerization of ethylene.

23. The process of claim 21 wherein the second catalyst is H-ZSM-5 zeolite.

24. The process of claim 21 wherein reacting the first product stream in the catalytic reactor takes place at a temperature of about 275° C.

25. The process of claim 21 wherein said process produces a total yield of $C_{4+}$ hydrocarbon products in the range of about 60% to about 80%.

26. The process of claim 21 wherein said process produces a total yield of $C_{4+}$ nonaromatic hydrocarbons in the range of about 50% to about 60%.

27. The process of claim 21 further comprising removing water from the first product stream to decrease water partial pressure to about 2.4 Torr.

28. The process of claim 21 further comprising removing $CO_2$ from the first product stream.

29. The process of claim 21 further comprising providing means for removing by-products from the first product stream.

30. The process of claim 24 wherein the step of reacting methane and $O_2$ in the oxidative coupling reactor takes place at a temperature of about 800° C.

* * * * *